US00PP21614P3

(12) United States Plant Patent
Hart

(10) Patent No.: US PP21,614 P3
(45) Date of Patent: Jan. 11, 2011

(54) FEIJOA VARIETY NAMED 'ANATOKI'

(50) Latin Name: *Acca sellowiana*
Varietal Denomination: Anatoki

(76) Inventor: Roy Hart, 82 Trewavas St., Mouteka (NZ) 7120

( * ) Notice: Subject to any disclaimer, the term of this patent is extended or adjusted under 35 U.S.C. 154(b) by 0 days.

(21) Appl. No.: 12/378,015

(22) Filed: Feb. 10, 2009

(65) Prior Publication Data

US 2009/0158475 P1 Jun. 18, 2009

(51) Int. Cl.
*A01H 5/00* (2006.01)

(52) U.S. Cl. ..... Plt./156

(58) Field of Classification Search ..... Plt./156
See application file for complete search history.

(56) References Cited

U.S. PATENT DOCUMENTS

PP8,825 P 7/1994 Patterson et al.

OTHER PUBLICATIONS

UPOV ROM GTITM Computer Database, GTI Jouve Retrieval Software 2009/05 Citation for 'Anatoki'.*
US Plant Application Serial Number not yet assigned, for Feijoa Varity Named 'Kaiteri'.
US Plant Application Serial Number not yet assigned, for Feijoa Varity Named 'Kakariki'.

* cited by examiner

*Primary Examiner*—Wendy C. Haas
(74) *Attorney, Agent, or Firm*—Wells St. John P.S.

(57) ABSTRACT

A new feijoa variety designated by the varietal name 'Anatoki' is disclosed and which is characterized principally as to novelty by producing a large fruit which is ripe for harvesting on or about April 11 under the ecological conditions prevailing near Nelson, New Zealand.

2 Drawing Sheets

Botanical designation: *Acca sellowiana.*
Variety denomination: 'Anatoki'.

RELATED PATENT DATA

The present application claims priority from the New Zealand Plant Variety Rights Application Serial No. FEI011, which was filled Jun. 27, 2007.

BACKGROUND OF THE NEW VARIETY

The present invention relates to a new and distinct variety of feijoa '*Acca sellowiana*' and more specifically to a feijoa variety named 'Anatoki' which produces fruit for harvesting in the very early season, that is, from at least about Apr. 11, 2008 under the ecological conditions prevailing near Nelson, New Zealand.

It has long been recognized that it would be desirable to provide a feijoa variety that bears a crop earlier in the season than those varieties that it is most closely similar to, and under the ecological conditions prevailing near Nelson, New Zealand. In this regard, several well known and popular feijoa varieties are harvested in both the early and late seasons near Nelson, New Zealand. However, their respective fruit sizes are relatively small, on average, when compared to the large fruit size produced by the present variety of feijoa. More specifically, the variety of feijoa identified by the varietal name 'Opal Star' (U.S. Plant Pat. No. 8,825) is characterized by producing relatively small fruit (about 85 grams) during the late season, that is, from about May 16, 2008 under the ecological conditions prevailing near Nelson, New Zealand. Still further, the variety 'Apollo' (unpatented), produces an average sized fruit weighing about 100 grams, and which is ripe for harvesting about Apr. 18, 2008 under the same ecological conditions. Still further, the unpatented variety 'Triumph' produces a small fruit (about 85 grams) and which is ripe for harvesting about May 23, 2008 under the same ecological conditions. Yet further, the variety 'Unique' (unpatented) also produces a small fruit (about 85 grams), and which is ripe in the early season for harvesting, that is, on or about Apr. 18, 2008 under the conditions prevailing near Nelson, New Zealand. Moreover, the present variety is similar in some respects to the feijoa variety 'Kaiteri' (U.S. application Ser. No. 12/322,988), and which is ripe for harvesting in the very early season, that is, from on or about Apr. 4, 2008 near Nelson, New Zealand. Still further, the new variety is somewhat similar to the variety 'Kakariki' (U.S. application Ser. No. 12/378,017), and which produces a large fruit (about 100 grams) in the very early season from about Mar. 28, 2008 under the ecological conditions prevailing near Nelson, New Zealand. In contrast, the present variety is distinguishable therefrom, and characterized as to novelty by producing a large fruit (about 110 grams) in the very early season, that is, from at least about Apr. 11, 2008 under the ecological conditions prevailing near Nelson, New Zealand. In view of its early harvesting date and large size, the present variety provides a degree of commercial and consumer appeal not present with other known varieties.

ORIGIN AND SEXUAL REPRODUCTION

The present variety of feijoa was derived from a selective cross pollination of the unpatented feijoa variety 'Apollo' and an unnamed seedling which was conducted in the cultivated area of the Applicant's farm during the 1996 growing season. The present variety 'Anatoki' was first asexually propagated from cuttings taken from this first sexually reproduced plant. Subsequent thereto, it has been established that the asexually reproduced plants derived from these cuttings are true over successive generations. The present variety is unique and novel as to other varieties it is most closely similar to, by producing a large sized fruit having an average weight of about 110 grams, and which is ripe for harvesting and shipment on or about Apr. 11, 2008 under the ecological conditions prevailing near Nelson, New Zealand.

BRIEF DESCRIPTION OF THE DRAWINGS

The accompanying drawings which are provided are color photographs of the new variety of feijoa. The colors in these photographs are as nearly true as is reasonably possible on a color representation of this type. Due to chemical development, processing, and printing, the leaves and fruit depicted in these photographs may or may not be accurate when compared to the actual specimen. For this reason, future color references should be made to the color plates as provided by The Royal Horticulture Society Colour Charts (1995 Edition).

NOT A COMMERCIAL WARRANTY

Figure 1:
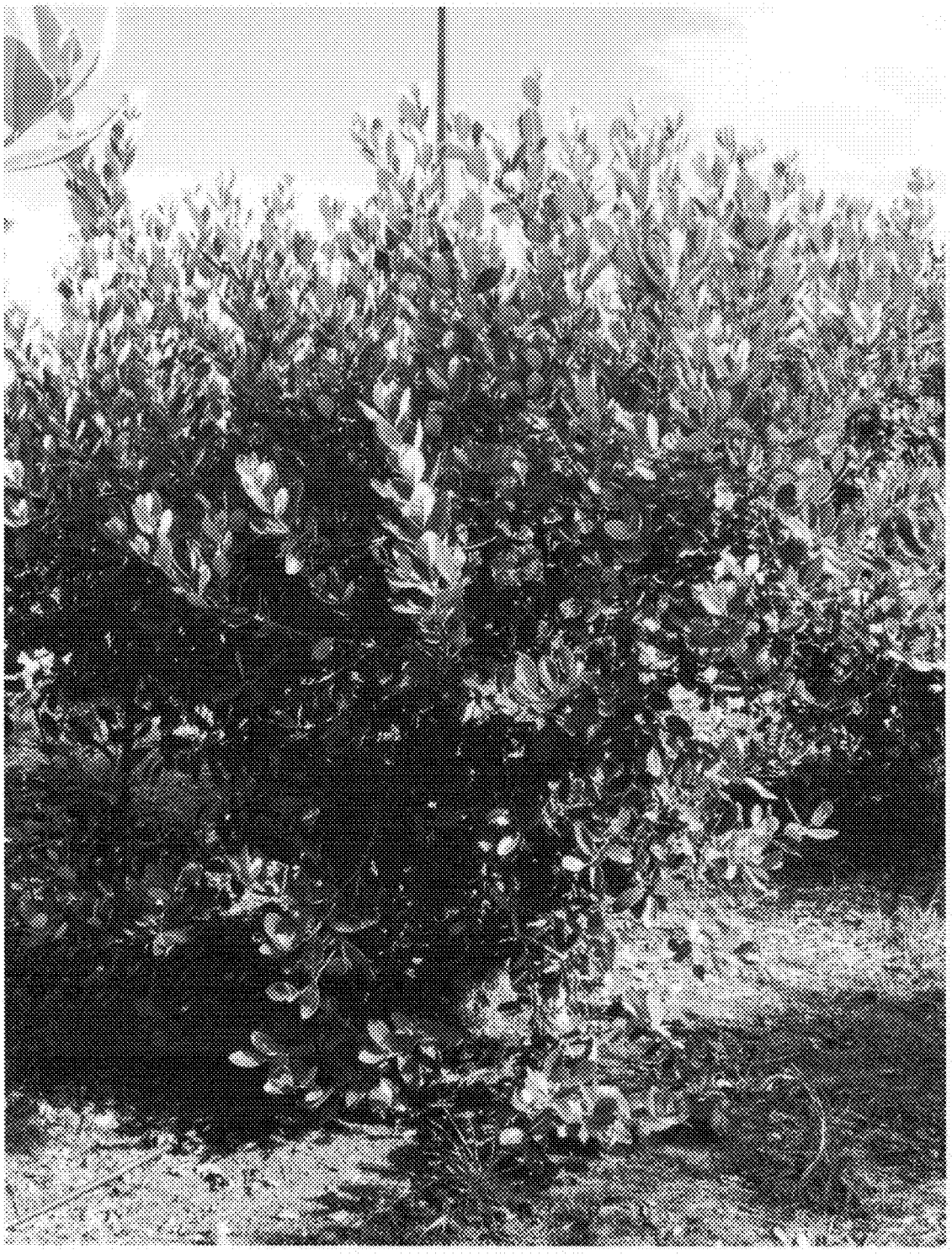
FIG. 1 is a color photograph depicting the new variety of feijoa growing on it's own roots and which is approximately 4 years old.
Figure 2:
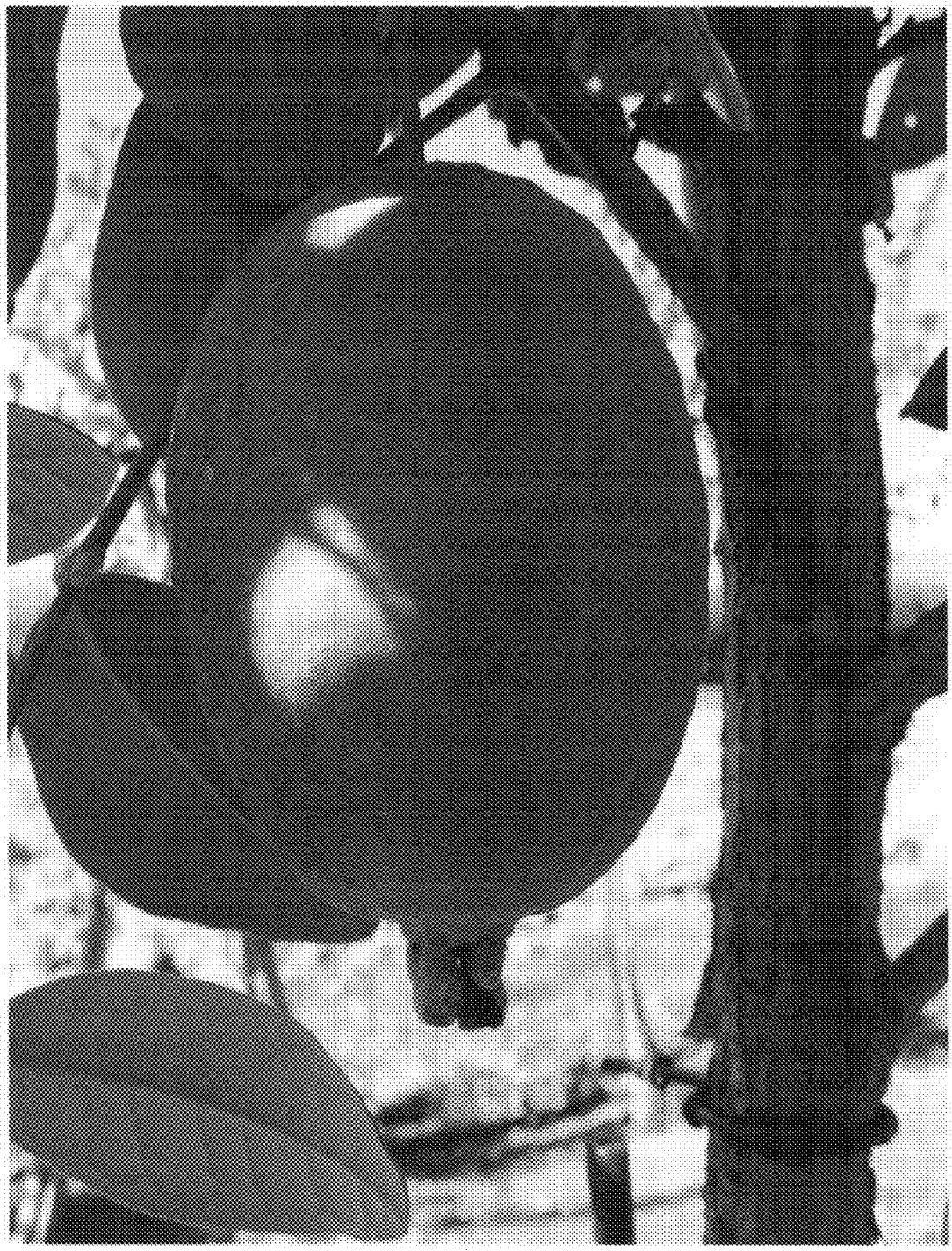
FIG. 2 is a photograph of a typical fruit sufficiently matured for harvesting.

The following detailed description has been prepared to solely comply with the provisions of 35 USC §112, and does not constitute a commercial warranty (either expressed or implied), that the present variety will, in the future, display the botanical or other varietal characteristics as set forth in this application. Therefore, this disclosure may not be relied upon to support any future legal claims, which include, but are not limited to breach of warranty of merchantability, fitness for any particular purpose, or non-infringement which is directed in whole, or in part, to the present variety.

DETAILED DESCRIPTION

TREE

*Origin.*—The present variety was selected from a selective cross-pollination of the unpatented feijoa variety 'Apollo' and an unnamed seedling in 2004. Subsequent asexual reproductions of the present variety have been shown to remain true to type over successive generations.
*Vigor.*—Considered average for the variety.
*Tree form.*—Ramified.
*Growth habit.*—Considered spreading.
*Size.*—About 2 meters in height.
*Crown diameter.*—About 2 meters when measured at a height of about 1 meter above the ground.

TRUNK

*Size.*—About 7 cm. in diameter when measured at a distance of about 20 cm. above the ground.
*Bark texture.*—Rough and considered somewhat flaky.
*Bark color.*—Grey-brown (RHS 199B).

LEAVES

*Leaf length.*—On average about 70 mm.
*Leaf width.*—On average about 35 mm.
*Leaf shape.*—Elliptical.
*Marginal form.*—Considered straight.
*Leaf color.*—Upper surface — Green (RHS 139A).
*Leaf color.*—Lower surface — Grey-green (RHS 190C).

FLOWERS

*Number of flowers per cluster.*—4 or 5 are typically found per cluster.
*Petals.*—Quantity — 4.
*Petal color.*—Upper surface — White (RHS 155C).
*Petal color.*—Lower surface — Red-purple (RHS 65D).
*Sepals.*—Quantity — 4.
*Stamins.*—Quantity — Numerous.
*Stamins.*—Color — Red (RHS 45C).
*Pistil.*—Quantity — 1.
*Pistil.*—Color — Red (RHS 45A).
*Pollination.*—Generally — Considered self-infertile. The inventor has discovered that any feijoa variety that flowers at approximately the same time of the season appears to be a suitable pollinator.

FRUIT

*Size.*—At full commercial maturity, considered large and having an average weight of about 110 grams.
*Fruit length.*—On average, about 70 mm.
*Fruit width.*—On average, about 55 mm.
*Fruit shape.*—Generally speaking obovoid when considered in profile.
*Skin surface texture.*—Slightly irregularly bumpy.
*Skin color.*—Green (RHS 136C).
*Flesh texture.*—Generally considered soft and having a small amount of gritty flesh near the skin.
*Flesh flavor.*—Considered acidic and sweet. The flesh is aromatic.
*Brix.*—At the appropriate harvesting time, about 12 degrees.
*Flesh color.*—White (RHS 157C).
*Harvesting time.*—Considered very early under the ecological conditions prevailing near Nelson, New Zealand, that is beginning on or about Apr. 15. This date of harvesting is contingent upon the ambient environmental conditions prevailing at Nelson, New Zealand.
*Fruit use.*—For fresh local markets and processed consumption.
*Fruit storage.*—Typically, about 28 days at a temperature of 1 degree Celsius. The fruit of the present variety has a shelf life of about 2 to 7 days.

Although the new variety of feijoa possesses the described characteristics when grown under the ecological conditions prevailing at or near Nelson, New Zealand, it is to be understood that variations of the usual magnitude and characteristics incident to changes in growing conditions, fertilization, pruning and pest control are to be expected.

Having thus described and illustrated my new variety of feijoa plant, what I claim is new, and desire to secure by Plant Letters Patent is:

1. A new and distinct variety of feijoa as substantially shown and described and which is ripe for harvesting on or about April 11 under the ecological conditions prevailing near Nelson, New Zealand.

* * * * *